United States Patent
Lee et al.

(10) Patent No.: US 10,105,122 B2
(45) Date of Patent: Oct. 23, 2018

(54) ULTRASOUND DIAGNOSIS DEVICE, DISPLAY DEVICE DISPLAYING ULTRASOUND IMAGE, AND METHOD OF OPERATING ULTRASOUND DIAGNOSIS DEVICE

(71) Applicants: SAMSUNG MEDISON CO., LTD., Hongcheon-gun (KR); SAMSUNG ELECTRONICS CO., LTD., Suwon-si (KR)

(72) Inventors: Yun-hee Lee, Seoul (KR); Hee-won Kim, Seoul (KR); Mi-jeoung Ahn, Seoul (KR); Ho-san Han, Seoul (KR); Su-jin Kim, Yongin-si (KR)

(73) Assignees: SAMSUNG MEDISON CO., LTD., Hongcheon-gun (KR); SAMSUNG ELECTRONICS CO., LTD., Suwon-si (KR)

( * ) Notice: Subject to any disclaimer, the term of this patent is extended or adjusted under 35 U.S.C. 154(b) by 225 days.

(21) Appl. No.: 14/423,259

(22) PCT Filed: Aug. 22, 2013

(86) PCT No.: PCT/KR2013/007522
§ 371 (c)(1),
(2) Date: Feb. 23, 2015

(87) PCT Pub. No.: WO2014/030933
PCT Pub. Date: Feb. 27, 2014

(65) Prior Publication Data
US 2015/0297180 A1 Oct. 22, 2015

(30) Foreign Application Priority Data
Aug. 22, 2012 (KR) .......... 10-2012-0092000

(51) Int. Cl.
*A61B 8/00* (2006.01)
*A61B 8/14* (2006.01)
*A61B 8/08* (2006.01)

(52) U.S. Cl.
CPC .............. *A61B 8/4427* (2013.01); *A61B 8/14* (2013.01); *A61B 8/4444* (2013.01); *A61B 8/462* (2013.01);
(Continued)

(58) Field of Classification Search
CPC ....... A61B 8/4427; A61B 8/56; A61B 8/5207; A61B 8/4444; A61B 8/14; A61B 8/462; A61B 8/54; A61B 8/4472; A61B 8/585
(Continued)

(56) References Cited

U.S. PATENT DOCUMENTS 6,440,072 B1 8/2002 Schuman et al.
6,447,451 B1 9/2002 Wing et al.
(Continued)

FOREIGN PATENT DOCUMENTS

| | | |
|---|---|---|
| JP | 08-252250 A | 10/1996 |
| KR | 10-2010-0065720 A | 6/2010 |
| WO | 2006/030378 A1 | 3/2006 |

OTHER PUBLICATIONS

Communication dated Mar. 31, 2016, issued by the European Patent Office in counterpart European Application No. 13831803.5.
(Continued)

*Primary Examiner* — Sanjay Cattungal
(74) *Attorney, Agent, or Firm* — Sughrue Mion, PLLC

(57) ABSTRACT

Provided is an ultrasonic diagnostic apparatus, a display apparatus for displaying an ultrasonic image, and a method of operating the ultrasonic diagnostic apparatus. The ultrasonic diagnostic apparatus includes a first communication unit configured to communicate with a probe, a second
(Continued)

communication unit configured to communicate with a display apparatus, and a controller configured to communicate with an ultrasonic diagnostic application when the ultrasonic diagnostic apparatus is in communication with the probe and the display apparatus.

9 Claims, 5 Drawing Sheets

(52) U.S. Cl.
CPC .............. *A61B 8/5207* (2013.01); *A61B 8/54* (2013.01); *A61B 8/56* (2013.01); *A61B 8/4472* (2013.01); *A61B 8/585* (2013.01)

(58) Field of Classification Search
USPC .................................................. 600/437–469
See application file for complete search history.

(56) References Cited

U.S. PATENT DOCUMENTS

| | | | |
|---|---|---|---|
| 6,980,419 B2 | 12/2005 | Smith et al. | |
| 2003/0125629 A1* | 7/2003 | Ustuner | A61B 8/00 600/459 |
| 2005/0251035 A1* | 11/2005 | Wong | A61B 8/00 600/437 |
| 2008/0132786 A1* | 6/2008 | Asai | A61B 8/14 600/437 |
| 2008/0295599 A1* | 12/2008 | Clasen | G01B 17/025 73/599 |
| 2009/0270727 A1 | 10/2009 | Zhao et al. | |
| 2010/0145195 A1 | 6/2010 | Hyun | |
| 2010/0191121 A1* | 7/2010 | Satoh | A61B 8/00 600/459 |
| 2011/0054296 A1* | 3/2011 | McCarthy | A61B 5/742 600/407 |
| 2012/0095459 A1* | 4/2012 | Callas | A61B 18/14 606/41 |
| 2012/0316407 A1* | 12/2012 | Anthony | A61B 8/4209 600/301 |
| 2014/0378964 A1* | 12/2014 | Pearson | A61B 18/1477 606/41 |
| 2015/0297180 A1* | 10/2015 | Lee | A61B 8/4427 600/443 |

OTHER PUBLICATIONS

Communication dated Jun. 29, 2015, issued by the Korean Intellectual Property Office in counterpart Korean Application No. 10-2013-0099887.
International Search Report for PCT/KR2013/007522 dated Dec. 11, 2013 [PCT/ISA/210].
Written Opinion for PCT/KR2013/007522 dated Dec. 11, 2013 [PCT/ISA/237].
Communication from the Korean Intellectual Property Office dated Dec. 23, 2014 in a counterpart Korean application No. 10-2013-0099887.

* cited by examiner

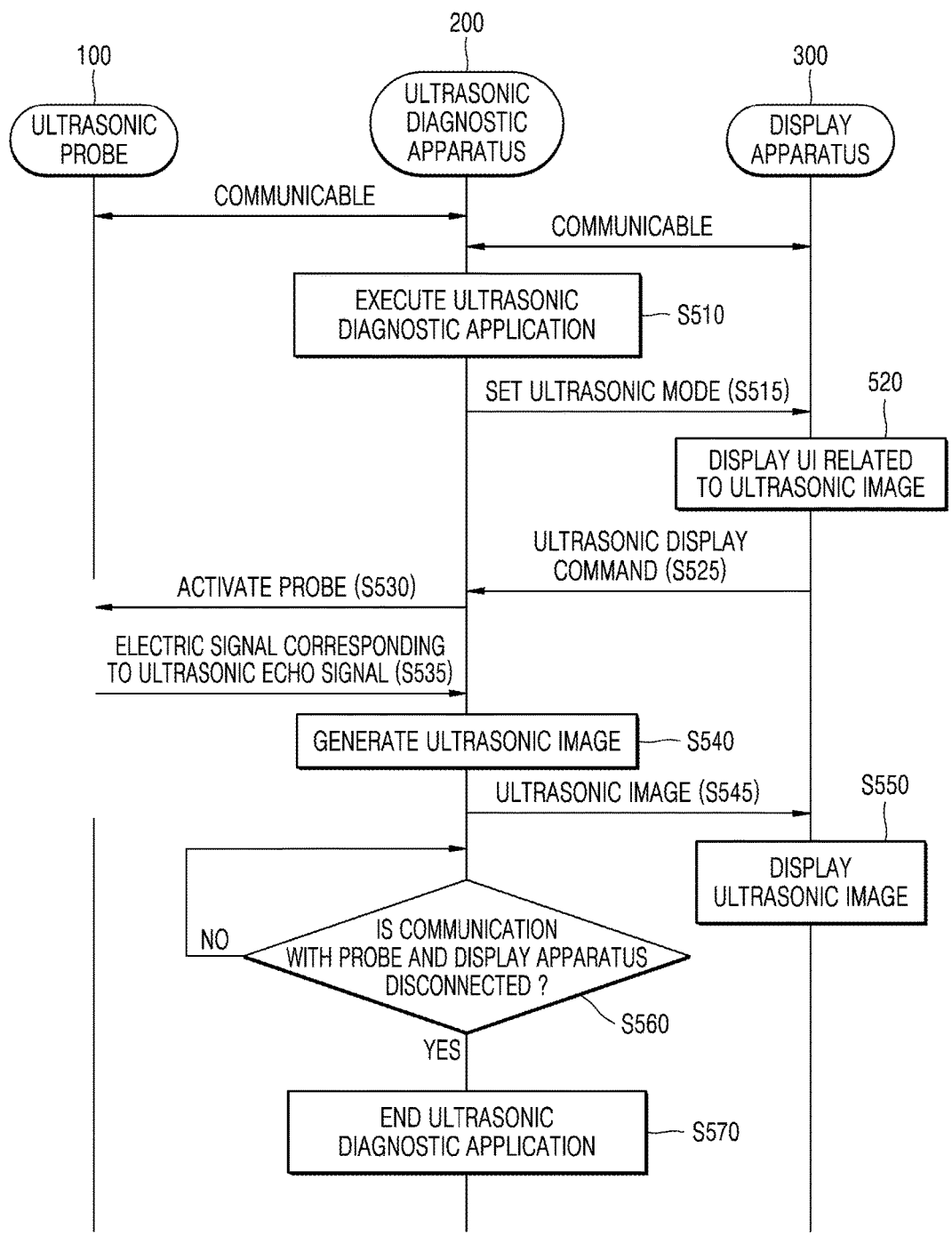

ULTRASOUND DIAGNOSIS DEVICE, DISPLAY DEVICE DISPLAYING ULTRASOUND IMAGE, AND METHOD OF OPERATING ULTRASOUND DIAGNOSIS DEVICE

TECHNICAL FIELD

The present inventive concept relates to an ultrasonic diagnostic apparatus, a display apparatus for displaying an ultrasonic image, and a method of operating the ultrasonic diagnostic apparatus.

BACKGROUND ART

Generally, an ultrasonic diagnostic apparatus irradiates ultrasonic waves to an examination target, such as a person or an animal, displays a cross-sectional image of tissues in the examination target by detecting an echo signal reflected from the examination target, and provides information required to diagnose the examination target.

Such an ultrasonic diagnostic apparatus does not expose a person to radiation, such as X-rays, and is stable, and thus is widely used along with other image diagnostic apparatuses, such as an X-ray diagnostic apparatus, a computerized tomography (CT) scanner, a magnetic resonance imaging (MRI) apparatus, and a nuclear medicine diagnostic apparatus.

Since the ultrasonic diagnostic apparatus is very large and heavy, the ultrasonic diagnostic apparatus is fixed at a certain location. Even a small ultrasonic system weighs at least 10 kg, and thus it cannot be easily moved or carried. Accordingly, a portable ultrasonic diagnostic apparatus needs to be developed.

DETAILED DESCRIPTION OF THE INVENTION

Technical Problem

The present inventive concept provides a portable ultrasonic diagnostic apparatus using a display unit of an external apparatus.

The present inventive concept also provides a small ultrasonic diagnostic apparatus, a system including the small ultrasonic diagnostic apparatus, and a method of operating the small ultrasonic diagnostic apparatus.

Technical Solution

According to an aspect of the present inventive concept, there is provided an ultrasonic diagnostic apparatus including: a first communication unit configured to communicate with a probe; a second communication unit configured to communicate with a display apparatus; and a controller configured to execute an ultrasonic diagnostic application when the ultrasonic diagnostic apparatus communicates with the probe and the display apparatus.

The controller may be further configured to execute the ultrasonic diagnostic application by setting a mode of the display apparatus to an ultrasonic mode.

The ultrasonic mode may be a mode wherein the display apparatus is configured to perform a function related to displaying an ultrasonic image.

The controller may be further configured to execute the ultrasonic diagnostic application by activating the probe.

The ultrasonic diagnostic apparatus may further include an image processor configured to generate an ultrasonic image in response to an electric signal corresponding to an ultrasonic echo signal received from the probe.

When communication with at least one of the probe and the display apparatus is disconnected, the controller may be further configured to provide a notification indicating the disconnected communication.

When a certain period of time passes after the communication is disconnected, the controller may be further configured to end the ultrasonic diagnostic application.

The ultrasonic diagnostic apparatus may be portable.

The ultrasonic diagnostic apparatus may further include: a body to which the display apparatus is mounted; and a swing portion connected to the body and configured to swing with respect to the body.

The first communication unit, the second communication unit, and the controller may be provided in the body.

The swing portion may have a quadrangular ring shape.

The swing portion may include: a connection portion connected to the body; a first end portion that supports the ultrasonic diagnostic apparatus together with the body; and a second end portion disposed opposite the first end portion based on the connection portion.

The connection portion may be convexly curved towards the body.

The second end portion may approach the body when the first end portion recedes from the body, and the second end portion may recede from the body when the first end portion approaches the body.

The display apparatus may be a portable terminal including a display unit configured to display an ultrasonic image.

According to another aspect of the present inventive concept, there is provided a display apparatus for displaying an ultrasonic image, the display apparatus including: a communication unit configured to communicate with an ultrasonic diagnostic apparatus; a display unit configured to display an ultrasonic image received from the ultrasonic diagnostic apparatus; and a controller configured to set a mode of the display apparatus to an ultrasonic mode when the display apparatus is in communication with the ultrasonic diagnostic apparatus.

When a communication event is received from an external apparatus other than the ultrasonic diagnostic apparatus during the ultrasonic mode, the controller may be further configured to provide a notification indicating that the communication event is received.

The controller may be further configured to receive a user command about the ultrasonic image from the ultrasonic diagnostic apparatus and to display the user command on the display unit.

When a user command about the ultrasonic image is received, the controller may be further configured to transmit the user command to the ultrasonic diagnostic apparatus through the communication unit, receive a result corresponding to the user command from the ultrasonic diagnostic apparatus, and display the result on the display unit.

When communication with the ultrasonic diagnostic apparatus is disconnected, the controller may be further configured to set a mode of the display apparatus to a mode before the ultrasonic mode is set or to an initial mode of the display apparatus.

According to another aspect of the present inventive concept, there is provided a method of operating an ultrasonic diagnostic apparatus, the method including: setting a mode of the display apparatus to an ultrasonic mode when the ultrasonic diagnostic apparatus is in communication with a probe and a display apparatus; generating an ultrasonic image in response to an electric signal corresponding to an echo signal of ultrasonic waves received from the probe; and transmitting the ultrasonic image to the display apparatus.

Advantageous Effects

An ultrasonic diagnostic apparatus according to the present inventive concept may be miniaturized since the ultrasonic diagnostic apparatus uses a display unit of an external device.

Also, since the ultrasonic diagnostic apparatus according to the present inventive concept executes an application required for ultrasonic diagnosis, a display apparatus does not require a separate application for displaying an ultrasonic image, and thus various types of display apparatuses may be applied to an ultrasonic diagnostic system.

DESCRIPTION OF THE DRAWINGS

FIG. 9 is a diagram for describing a method of operating an ultrasonic diagnostic system, according to an embodiment of the present inventive concept.

MODE OF THE INVENTION

Figure 1:
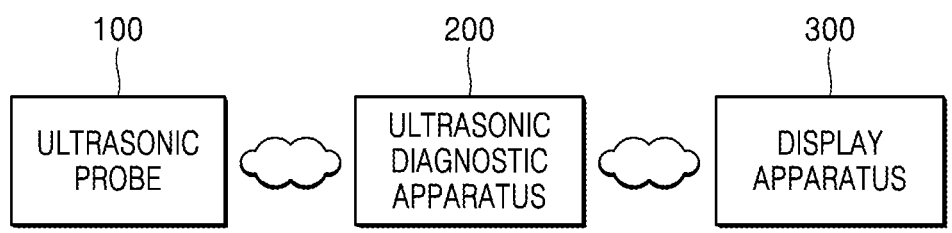
FIG. 1 is a block diagram of an ultrasonic diagnostic system according to an embodiment of the present inventive concept.

Hereinafter, an ultrasonic diagnostic apparatus, an ultrasonic diagnostic system including the same, and a method of operating an ultrasonic system according to exemplary embodiments of the present inventive concept will be described in detail with reference to the accompanying drawings. Those components that are the same or are in correspondence are rendered the same reference numeral regardless of the figure number, and redundant explanations are omitted.

Figure 2:
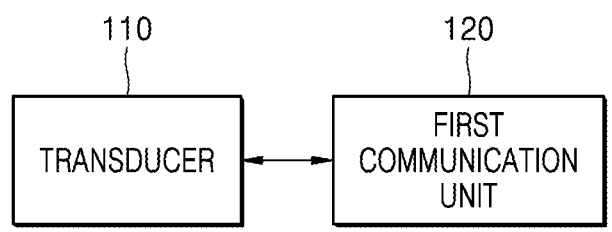
FIG. 2 is a block diagram of an ultrasonic probe of the ultrasonic diagnostic system of FIG. 1.
Figure 3:
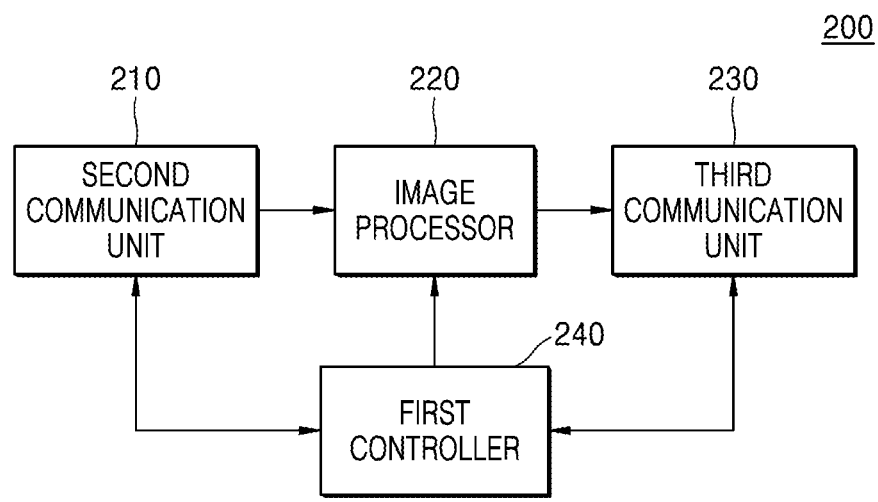
FIG. 3 is a block diagram of an ultrasonic diagnostic apparatus of the ultrasonic diagnostic system of FIG. 1.
Figure 4:
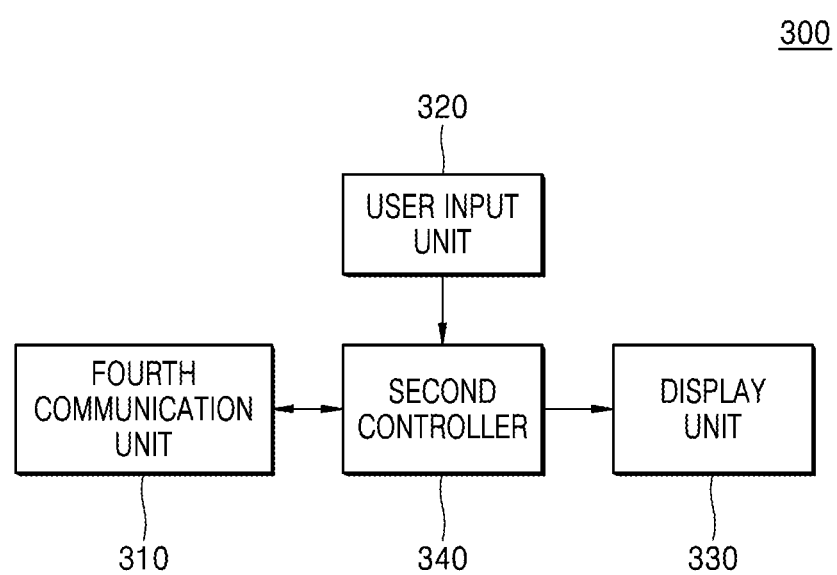
FIG. 4 is a block diagram of a display apparatus of the ultrasonic diagnostic system of FIG. 1.

FIG. 1 is a block diagram of an ultrasonic diagnostic system 10 according to an embodiment of the present inventive concept, FIG. 2 is a block diagram of an ultrasonic probe 100 of the ultrasonic diagnostic system 10 of FIG. 1, FIG. 3 is a block diagram of an ultrasonic diagnostic apparatus 200 of the ultrasonic diagnostic system 10 of FIG. 1, and FIG. 4 is a block diagram of a display apparatus 300 of the ultrasonic diagnostic system 10 of FIG. 1.

As shown in FIG. 1, the ultrasonic diagnostic system 10 may include the ultrasonic probe 100 that irradiates ultrasonic waves to an examination target and receives an ultrasonic echo signal from the examination target, the ultrasonic diagnostic apparatus 200 that generates an ultrasonic image from an electric signal corresponding to the ultrasonic echo signal, and the display apparatus 300 that displays the ultrasonic image.

The ultrasonic probe 100 according to an embodiment of the present inventive concept may be at least one of 1 dimensional (1D), 1.5D, 2D (matrix), and 3D probes. The ultrasonic diagnostic apparatus 200 has a size that is grabbable and portable by a user, and the display apparatus 300 may also be a portable terminal, such as a mobile phone or a tablet personal computer (PC).

As shown in FIG. 2, the ultrasonic probe 100 includes a transducer 110 that mutually changes an electric signal and ultrasonic waves, and a first communication unit 120 that is communicable with the ultrasonic diagnostic apparatus 200. The transducer 110 changes an electric signal to ultrasonic waves to be transmitted to the examination target, and changes an ultrasonic echo signal received from the examination target to an electric signal. The transducer 110 may include a plurality of unit transducers 110 for mutually changing ultrasonic waves and an electric signal. The plurality of unit transducers 110 may be in a 1D array form or a 2D array form.

The transducer 110 may be a piezoelectric micromachined ultrasonic transducer (pMUT) that mutually changes ultrasonic waves and an electric signal via pressure change while vibrating, a capacitive micromachined ultrasonic transducer (cMUT) that mutually changes ultrasonic waves and an electric signal via capacity change, a magnetic micromachined ultrasonic transducer (mMUT) that mutually changes ultrasonic waves and an electric signal via magnetic field change, or an optical ultrasonic detector that mutually changes ultrasonic waves and an electric signal via change of optical characteristics.

The first communication unit 120 enables communication between the ultrasonic probe 100 and the ultrasonic diagnostic apparatus 200. The first communication unit 120 may communicate with the ultrasonic diagnostic apparatus 200 via wires or wirelessly. For example, the first communication unit 120 may be a female and male type connector disposed at one end of a cable extending from a housing (not shown) of the ultrasonic probe 100. Alternatively, the first communication unit 120 may be a Wi-Fi module.

Meanwhile, as shown in FIG. 3, the ultrasonic diagnostic apparatus 200 may include a second communication unit 210 communicable with the ultrasonic probe 100, an image processor 220 that generates an ultrasonic image by using a signal received from the ultrasonic probe 100, a third communication unit 230 that communicates with the display apparatus 300, for example, by transmitting the ultrasonic image to the display apparatus 300, and a first controller 240 that not only controls each component of the ultrasonic diagnostic apparatus 200, but also controls the ultrasonic probe 100 and the display apparatus 300.

In detail, the second communication unit 210 may communicate with the first communication unit 120 in a communication manner corresponding to the first communication unit 120. For example, when the first communication unit 120 is a female and male type connector, the second communication unit 210 may also be a female and male type connector combinable to the first communication unit 120. Alternatively, when the first communication unit 120 is a Wi-Fi module, the second communication unit 210 may also be a Wi-Fi module.

The image processor 220 may generate an ultrasonic image by processing an electric signal corresponding to an ultrasonic echo signal received from the ultrasonic probe 100. When an electric signal corresponding to an ultrasonic echo signal is an analog signal, the image processor 220 may change the analog signal to a digital signal, form a reception focused signal by receiving and focusing the digital signal while considering the unit transducer 110 and a focus point, and generate an ultrasonic image based on the reception focused signal.

The ultrasonic image generated as such may be at least one of a brightness mode (B-mode) image showing a size of an ultrasonic echo signal reflected from an object in brightness, a Doppler mode image showing an image of a moving object in a spectrum form by using a Doppler effect, a motion mode (M-mode) image showing movement of an object according to time at a certain location, an elastic mode image showing, as an image, a reaction difference of an object when compression is applied and not applied, and a color mode (C-mode) image showing a speed of a moving object in color by using a Doppler effect.

The image processor 220 may include one or more processors. A processor may be an array of a plurality of logic gates, or a combination of a general-purpose microprocessor and a memory storing a program executable by the general-purpose microprocessor. However, it would be obvious to one of ordinary skill in the art that the image processor 220 may be realized in any type of hardware. A processor performing one function of the image processor 220 may be disposed in the ultrasonic probe 100. For example, an analog digital converter that changes an analog signal to a digital signal may be disposed in the ultrasonic probe 100, and processors performing other functions of the image processor 220 may be disposed in an image diagnostic apparatus. Alternatively, when a reception focused signal is repeatedly formed a plurality of times, a partial processor forming a reception focused signal may be disposed in the ultrasonic probe 100.

The third communication unit 230 enables communication between the display apparatus 300 and the ultrasonic diagnostic apparatus 200. The third communication unit 230 may communicate with the display apparatus 300 via wires or wirelessly. For example, the third communication unit 230 may be realized as a port formed on a housing of the ultrasonic diagnostic apparatus 200. Alternatively, the third communication unit 230 may be realized as a Wi-Fi module.

The first controller 240 may control not only each component of the ultrasonic diagnostic apparatus 200, but also the ultrasonic probe 100 and the display apparatus 300. For example, when the display apparatus 300 and the ultrasonic probe 100 are communicable with the ultrasonic diagnostic apparatus 200, the first controller 240 may execute an ultrasonic diagnostic application. Accordingly, the first controller 240 may change a mode of the display apparatus 300 to an ultrasonic mode and activate the ultrasonic probe 100. Also, the first controller 240 may control the ultrasonic probe 100 so as to receive an electric signal corresponding to an ultrasonic echo signal from the ultrasonic probe 100, control the image processor 220 to generate an ultrasonic image, and control the display apparatus 300 to display the ultrasonic image.

Moreover, the first controller 240 may control the display apparatus 300 such that a user interface for receiving a user command for ultrasonic diagnosis is displayed on the display apparatus 300, and control the ultrasonic probe 100, the ultrasonic diagnostic apparatus 200, and the display apparatus 300 according to a user command received through the display apparatus 300.

As shown in FIG. 4, the display apparatus 300 may include a fourth communication unit 310 communicable with the ultrasonic diagnostic apparatus 200, a user input unit 320 that receives a user command for ultrasonic diagnosis, a display unit 330 that displays an ultrasonic image, and a second controller 340 that controls overall operations of the display apparatus 300 under control of the ultrasonic diagnostic apparatus 200.

The fourth communication unit 310 enables communication between the display apparatus 300 and the ultrasonic diagnostic apparatus 200. The fourth communication unit 310 may communicate with the display apparatus 300 via wires or wirelessly. For example, the third communication unit 230 may be realized as a port formed on a housing of the display apparatus 300. Alternatively, the third communication unit 230 may be realized as a Wi-Fi module.

A user generates input data for controlling operations of the ultrasonic diagnostic apparatus 200 by using the user input unit 320. The user input unit 320 may be a keypad, a dome switch, a touch pad (static pressure type or electrostatic type), a jog wheel, or a jog switch. In detail, the display unit 330 may be configured as a touch screen by forming a mutual layer structure with a touch pad.

The display unit 330 displays information processed by the ultrasonic diagnostic apparatus 200. For example, the display unit 330 may display an ultrasonic image. As described above, when the display unit 330 is configured as a touch screen by forming a mutual layer structure with a touch pad, the display unit 330 may also be used as an input device as well as an output device. The display unit 330 may include at least one of a liquid crystal display, a thin film transistor-liquid crystal display, an organic light-emitting diode, a flexible display, and a 3D display. Also, the ultrasonic diagnostic apparatus 200 may include at least two display units 330 according to a structure.

The touch screen may be configured such that not only a location and an area of a touch input are detected, but also pressure of the touch input is detected. Also, the touch screen may be configured such that not only a real-touch is detected, but also a proximity touch is detected.

The second controller 340 controls overall operations of the display apparatus 300, and when the display apparatus 300 is communicable with the ultrasonic diagnostic apparatus 200, may control the display apparatus 300 under control of the first controller 240 of the ultrasonic diagnostic apparatus 200.

For example, when a control signal for setting a mode of the display apparatus 300 to an ultrasonic mode is received from the first controller 240 after the display apparatus 300 and the ultrasonic diagnostic apparatus 200 are communicable with each other, the second controller 340 may set the mode of the display apparatus 300 to an ultrasonic mode. Also, upon receiving a communication event from an external apparatus other than the ultrasonic diagnostic apparatus 200 while the display apparatus 300 is in the ultrasonic mode, the second controller 340 may provide a notification indicating that the communication event is received without executing a program corresponding to the communication event. The notification may be provided in sound or in message. Here, the communication event may be a message, a voice call, or a video call received by the display apparatus 300.

Also, upon receiving a user interface related to an ultrasonic image from the ultrasonic diagnostic apparatus 200, the second controller 340 may display the user interface on the display unit 330. Moreover, upon receiving a user command related to the ultrasonic image from the user input unit 320, the second controller 340 may transmit the user command to the ultrasonic diagnostic apparatus 200 through the third communication unit 230, receive a result corresponding to the user command from the ultrasonic diagnostic apparatus 200, and display the result on the display unit 330.

Also, when communication with the ultrasonic diagnostic apparatus 200 is disconnected, the second controller 340 may set the mode of the display apparatus 300 to a mode before the ultrasonic mode is set or to an initial mode of the display apparatus 300. For example, the second controller 340 may provide a notification indicating that the communication with the ultrasonic diagnostic apparatus 200 is disconnected and change the mode of the display apparatus 300 after a certain period of time.

Also, when only the display apparatus 300 is connected to the ultrasonic diagnostic apparatus 200, the second controller 340 may provide a notification requesting connection to the ultrasonic probe 100 under control of the first controller 240. In detail, when the ultrasonic diagnostic apparatus 200 is communicable with the display apparatus 300 through the third communication unit 230 but is not communicable with the ultrasonic probe 100 through the second communication unit 210, the first controller 240 may generate a notification requesting connection to the ultrasonic probe 100 and transmit the notification to the display apparatus 300, and the second controller 340 of the display apparatus 300 may provide the notification.

Figure 5:
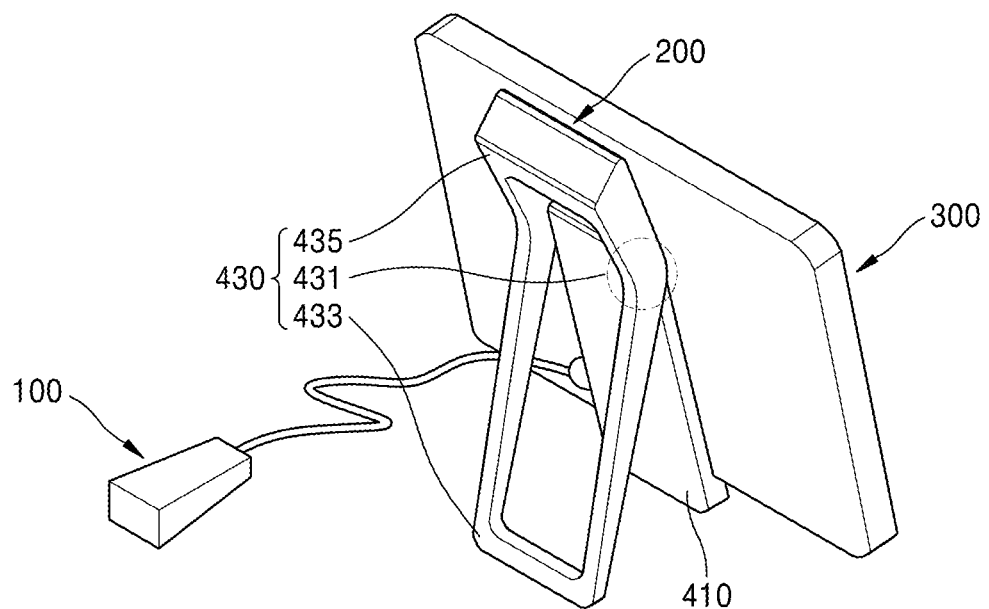
FIG. 5 is a view of an outer shape of the ultrasonic diagnostic apparatus of FIG. 3.
Figure 6:
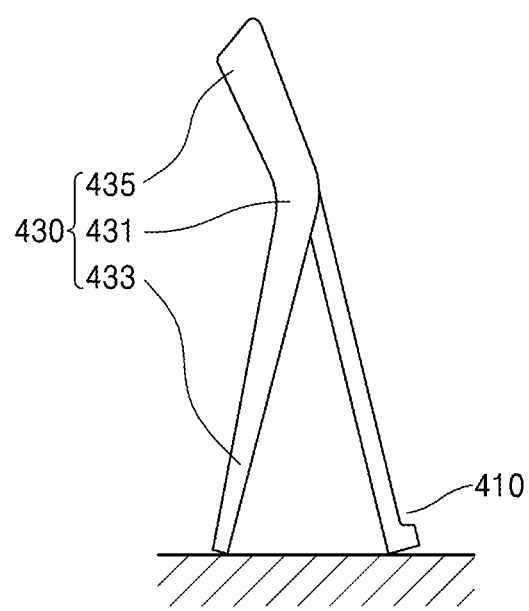
FIG. 6 is a cross-sectional view of the ultrasonic diagnostic apparatus in an upright position.
Figure 7:
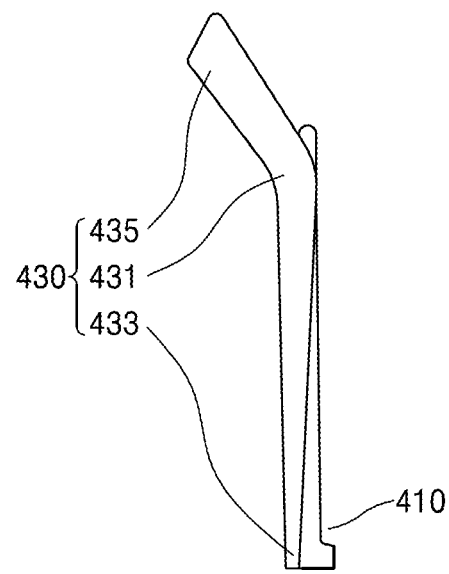
FIG. 7 is a cross-sectional view of the ultrasonic diagnostic apparatus in a folded position.
Figure 8:
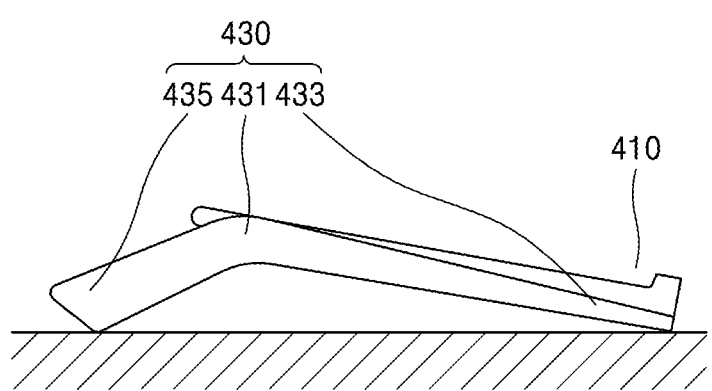
FIG. 8 is a cross-sectional view of the ultrasonic diagnostic apparatus in another folded position.

FIG. 5 is a view of an outer shape of the ultrasonic diagnostic apparatus 200 of FIG. 3, FIG. 6 is a cross-sectional view of the ultrasonic diagnostic apparatus 200 in a standing position, FIG. 7 is a cross-sectional view of the ultrasonic diagnostic apparatus 200 in a folded position, and FIG. 8 is a cross-sectional view of the ultrasonic diagnostic apparatus 200 in another folded position.

As shown in FIGS. 5 through 8, the ultrasonic diagnostic apparatus 200 includes a body 410 on which the display apparatus 300 is mounted, and a swing portion 430 having a partial region contacting the body 410 and swingable based on the body 410. Functional blocks of the ultrasonic diagnostic apparatus 200, i.e., the second communication unit 210, the third communication unit 230, the image processor 220, and the first controller 240, may be embedded in the body 410. In some cases, the second communication unit 210 and the third communication unit 230 may be exposed outside the body 410 as connectors.

The swing portion 430 includes a connection portion 431 connected to the body 410, a first end portion 433 supporting the ultrasonic diagnostic apparatus 200 together with the body 410, and a second end portion 435 disposed opposite to the first end portion 433 based on the connection portion 431. The connection portion 431 is convexly curved towards the body 410. Also, the connection portion 431, the first end portion 433, and the second end portion 435 may be integrally formed. Accordingly, the second end portion 435 may approach the body 410 when the first end portion 433 recedes from the body 410, and the second end portion 435 may recede from the body 410 when the first end portion 433 approaches the body 410.

The first end portion 433 supports the ultrasonic diagnostic apparatus 200 together with the body 410. For example, the first end portion 433 may move in a direction away from the body 410 based on the connection portion 431. Also, the ultrasonic diagnostic apparatus 200 may be fixed to a certain location, such as a floor, by using a distance between the body 410 and the first end portion 433. As such, the ultrasonic diagnostic apparatus 200 may stand as shown in FIG. 6. When the distance between the body 410 and the first end portion 433 increases, an angle between a mounting portion of the ultrasonic diagnostic apparatus 200 and the floor may decrease.

On the other hand, the second end portion 435 may approach the body 410 when the first end portion 433 recedes from the body 410. Also, the second end portion 435 may recede from the body 410 when the first end portion 433 approaches the body 410. Thus, as shown in FIG. 7, the ultrasonic diagnostic apparatus 200 may be folded. A user may hold the second end portion 435 while the ultrasonic diagnostic apparatus 200 is folded, and thus the second end portion 435 may operate as a handle of the ultrasonic diagnostic apparatus 200.

Moreover, while the ultrasonic diagnostic apparatus 200 is folded, the first and second end portions 433 and 435 may support the body 410. For example, as shown in FIG. 8, since the first and second end portions 433 and 435 maintain an angle within 180° based on the connection portion 431 while the first end portion 433 is folded towards the body 410, the body 410 may be supported.

The swing portion 430 may have a quadrangular ring shape. When the swing portion 430 has a rectangular ring shape, the swing portion 430 may satisfactorily support the ultrasonic diagnostic apparatus 200 and the user may easily hold the ultrasonic diagnostic apparatus 200. However, a shape of the swing portion 430 is not limited thereto. The swing portion 430 may have a triangular shape or a shape formed by two trapezoids that inversely contact each other.

In the current embodiment, the ultrasonic diagnostic application is executed when the ultrasonic probe 100 and the display apparatus 300 are communicable with the ultrasonic diagnostic apparatus 200, but an embodiment is not limited thereto. The ultrasonic diagnostic application may be executed when the ultrasonic diagnostic apparatus 200 is erected as shown in FIG. 6. For example, when the ultrasonic diagnostic apparatus 200 is erected, the first controller 240 may execute the ultrasonic diagnostic application and provide a notification requesting to mount the ultrasonic probe 100 and the display apparatus 300 on a surface of the body 410.

FIG. 9 is a diagram for describing a method of operating the ultrasonic diagnostic system 10, according to an embodiment of the present inventive concept.

When the ultrasonic probe 100 and the display apparatus 300 are communicable, the first controller 240 of the ultrasonic diagnostic apparatus 200 executes the ultrasonic diagnostic application, in operation S510. Then, the first controller 240 of the ultrasonic diagnostic apparatus 200 sets a mode of the display apparatus 300 to the ultrasonic mode in operation S515, and display a user interface related to an ultrasonic image on the display unit 330 of the display apparatus 300 in operation S520. The ultrasonic mode is a mode the display apparatus 300 performs a function related to displaying of an ultrasonic image.

When only one of the ultrasonic probe 100 and the display apparatus 300 is communicable, the first controller 240 of the ultrasonic diagnostic apparatus 200 may provide a notification that only one of the ultrasonic probe 100 and the display apparatus 300 is communicable. The notification may be provided through the display apparatus 300 or through the body 410. When the notification is provided through the body 410, the notification may be realized by lighting a light-emitting diode (LED).

Upon receiving a user command for executing ultrasonic diagnosis from the display apparatus 300 in operation S525, the first controller 240 of the ultrasonic diagnostic apparatus 200 activates the ultrasonic probe 100 in operation S530.

Then, the ultrasonic probe 100 irradiates ultrasonic waves to an examination target, receives an ultrasonic echo signal from the examination target, generates an electric signal corresponding to the ultrasonic echo signal, and transmits the electric signal to the ultrasonic diagnostic apparatus 200, in operation S535. In the current embodiment, the ultrasonic probe 100 is activated when the user command for executing the ultrasonic diagnosis is received, but an embodiment is not limited thereto. The ultrasonic probe 100 may be activated without a separate user command when the ultrasonic probe 100 is communicable with the ultrasonic diagnostic apparatus 200.

Upon receiving the electric signal corresponding to the ultrasonic echo signal, the image processor 220 generates an ultrasonic image in operation S540. Then, the first controller 240 transmits the generated ultrasonic image to the display apparatus 300 through the third communication unit 230 in operation S545. Then, the second controller 340 of the display apparatus 300 may display the ultrasonic image on the display unit 330, in operation S550.

Meanwhile, when it is determined that communication with at least one of the ultrasonic probe 100 and the display apparatus 300 is disconnected in operation S560, the first controller 240 of the ultrasonic diagnostic apparatus 200 ends the ultrasonic diagnostic application in operation S570. When the connection with at least one of the ultrasonic probe 100 and the display apparatus 300 is disconnected, the first controller 240 may provide a notification indicating such disconnection and end the ultrasonic diagnostic application after a certain period of time. When the ultrasonic diagnostic apparatus 200 and the display apparatus 300 are communicable with each other while the notification is provided, the first controller 240 may transmit the notification to the display apparatus 300 and the display apparatus 300 may externally provide the notification. However, when the ultrasonic diagnostic apparatus 200 and the display apparatus 300 are not communicable with each other, the first controller 240 may directly provide the notification.

Various embodiments other than those described above are defined by appended claims. As the inventive concept allows for various changes and numerous embodiments, particular embodiments will be illustrated in the drawings and described in detail in the written description. However, this is not intended to limit the present inventive concept to particular modes of practice, and it will to be appreciated that all changes, equivalents, and substitutes that do not depart from the spirit and technical scope of the present inventive concept are encompassed in the present inventive concept.

The invention claimed is:

1. An ultrasonic diagnostic apparatus comprising:
   a first communication unit configured to communicate with an ultrasonic probe;
   a second communication unit configured to communicate with a display apparatus;
   a controller configured to execute an ultrasonic diagnostic application by activating the ultrasonic probe automatically after the ultrasonic diagnostic apparatus communicates with both the ultrasonic probe and the display apparatus;
   a body to which the display apparatus is mounted; and
   a swing portion connected to the body and configured to swing with respect to the body,
   the swing portion having a quadrangular ring shape, and comprising:
      a connection portion connected to the body,
      a first end portion that support the ultrasonic diagnostic apparatus together with the body, and
      a second end portion disposed opposite the first end portion,
   wherein the first end portion, the connection portion, and the second end portion are sequentially arrange, and the first and second end portion are disposed at an angle of less than 180° with respect to each other,
   wherein the controller generates a notification requesting connection to the ultrasonic probe and transmits the notification to the display apparatus when the ultrasonic diagnostic apparatus is in communication with the display apparatus but is not in communication with the ultrasonic probe, and
   wherein the first communication unit, the second communication unit, and the controller are provided in the body.

2. The ultrasonic diagnostic apparatus of claim 1, wherein the controller is further configured to execute the ultrasonic diagnostic application by setting a mode of the display apparatus to an ultrasonic mode.

3. The ultrasonic diagnostic apparatus of claim 2, wherein the ultrasonic mode is a mode wherein the display apparatus is configured to perform a function related to displaying an ultrasonic image.

4. The ultrasonic diagnostic apparatus of claim 1, further comprising an image processor configured to generate an ultrasonic image in response to an electric signal corresponding to an ultrasonic echo signal received from the ultrasonic probe.

5. The ultrasonic diagnostic apparatus of claim 1, wherein, when a predetermined period of time passes after the communication is disconnected, the controller is further configured to end the ultrasonic diagnostic application.

6. The ultrasonic diagnostic apparatus of claim 1, wherein the ultrasonic diagnostic apparatus is portable.

7. The ultrasonic diagnostic apparatus of claim 1, wherein the connection portion is convexly curved towards the body.

8. The ultrasonic diagnostic apparatus of claim 1, wherein the second end portion approaches the body when the first end portion recedes from the body, and
   the second end portion recedes from the body when the first end portion approaches the body.

9. The ultrasonic diagnostic apparatus of claim 1, wherein the display apparatus is a portable terminal comprising a display unit configured to display an ultrasonic image.

* * * * *